United States Patent [19]
Wang

[11] Patent Number: 5,464,983
[45] Date of Patent: Nov. 7, 1995

[54] METHOD AND APPARATUS FOR DETERMINING THE CONCENTRATION OF A GAS

[75] Inventor: Annie Q. Wang, Pittsburgh, Pa.

[73] Assignee: Industrial Scientific Corporation, Oakdale, Pa.

[21] Appl. No.: 222,825

[22] Filed: Apr. 5, 1994

[51] Int. Cl.$^6$ .................................................. G01N 21/59
[52] U.S. Cl. ............................................ 250/343; 356/437
[58] Field of Search .............................. 250/343; 356/437

[56] References Cited

U.S. PATENT DOCUMENTS

| | | | |
|---|---|---|---|
| 3,805,074 | 4/1974 | McCormack | 250/355 |
| 4,157,470 | 6/1979 | Kotaka et al. | 250/345 |
| 4,266,131 | 5/1981 | Ahjopalo et al. | 250/341 |
| 4,358,679 | 11/1982 | Lipoma | 250/252.1 |
| 4,560,875 | 12/1985 | Crowder | 250/343 |
| 4,596,931 | 6/1986 | Ehnholm et al. | 250/343 |
| 4,605,313 | 8/1986 | Kebabian | 374/121 |
| 4,687,934 | 8/1987 | Passaro et al. | 250/343 |
| 4,694,174 | 9/1987 | Erath | 250/348 |
| 4,709,150 | 11/1987 | Burough et al. | 250/338 |
| 4,937,448 | 6/1990 | Mantz et al. | 250/343 |
| 4,963,745 | 10/1990 | Maggard | 250/343 |
| 5,013,920 | 5/1991 | Asano et al. | 250/343 |
| 5,070,244 | 12/1991 | Simpson | 250/343 |
| 5,081,998 | 1/1992 | Yelderman et al. | 128/719 |
| 5,086,229 | 2/1992 | Rosenthal et al. | 250/341 |
| 5,132,538 | 7/1992 | Norris | 250/339 |
| 5,163,332 | 11/1992 | Wong | 73/863.23 |
| 5,223,714 | 6/1993 | Maggard | 250/343 |
| 5,349,189 | 9/1994 | Maggard | 250/339.07 |

FOREIGN PATENT DOCUMENTS

1-285841  11/1989  Japan ........................................ 356/437

Primary Examiner—Constantine Hannaher
Attorney, Agent, or Firm—Buchanan Ingersoll

[57] ABSTRACT

A method and apparatus for determining the concentration of a gas using nondispersive infrared absorption. The method includes measuring the output signal for a plurality of instantaneous time periods, calculating the change of the output signals (CS), calculating the change of the change of the output signal (CCS) which creates a pattern of CCS data and comparing the CCS data with corresponding CCS data for a known reference gas at a known concentration and at a range of known temperatures. The apparatus for determining the concentration of a known gas in a sample gas mixture is a gas chamber, a light source, a detector, a signal converter, and a data acquisition and microprocessor unit which measures the output signal and has a memory with a program to calculate the change of the signal (CS) and the change of the change of the signal (CCS), and compare the CCS data generated from the gas sample mixture to CCS data of known gases with known concentrations and at known temperature ranges.

16 Claims, 8 Drawing Sheets

METHOD AND APPARATUS FOR DETERMINING THE CONCENTRATION OF A GAS

FIELD OF THE INVENTION

This invention relates to a method and apparatus for determining the concentration of a known gas. The invention uses nondispersive infrared absorption and a method which is insensitive to a change in ambient temperature.

PROBLEM SOLVED BY THE INVENTION

Nondispersive infrared absorption (NDIR) has been considered one of the best methods for determining the concentration of gas because the method can be utilized in portable gas analyzers. All chemicals have bonds containing molecular vibration energy which correspond to a specific wavelength absorption spectrum. If you apply energy to a chemical, the energy having a wavelength specific to the wavelength absorption spectrum of the chemical will be absorbed. In our case, energy in the form of infrared radiation is applied to a gas. When the infrared radiation shines on a specific gas, the infrared radiation having a wavelength specific to the wavelength absorption spectrum of the specific gas is absorbed by the gas. A NDIR gas analyzer typically includes an infrared source such as an incandescent lamp, a chamber for containing a sample gas, and a detector having an optical band pass filter. The gas sample mixture is introduced into the chamber and light is passed through the chamber. The optical band pass filter only allows infrared light with wavelengths specific to the absorption spectrum of the gas being detected to pass to the detector. Hence, the detector only senses light having a wavelength in the wavelength absorption spectrum of the gas being detected. An electrical signal is produced by the detector when light is sensed by the detector. The signal is fed to an electronic circuit that converts the signal such that the signal is inversely proportional to the concentration of the gas being detected. The greater the concentration of the gas, the greater will be the absorption of the light. The greater the absorption of the light, the lesser the amount of light that will be detected by the detector. The lower the amount of light detected, the lower the output signal will be from the detector. Therefore, the amount of infrared light that is absorbed is directly proportional to the concentration of the gas, and the concentration of gas detected is inversely proportional to the magnitude of the output signal from the detector.

The detector usually is a thermally sensitive detector such as a thermopile. Because most of the infrared detectors are temperature sensitive, they not only react to the infrared light in the chamber but also to changes in ambient temperature. When a gas analyzer is used in the field, ambient temperature changes can significantly affect the sensitivity, stability and reliability of the gas analyzer when determining gas concentration.

Figure 1:
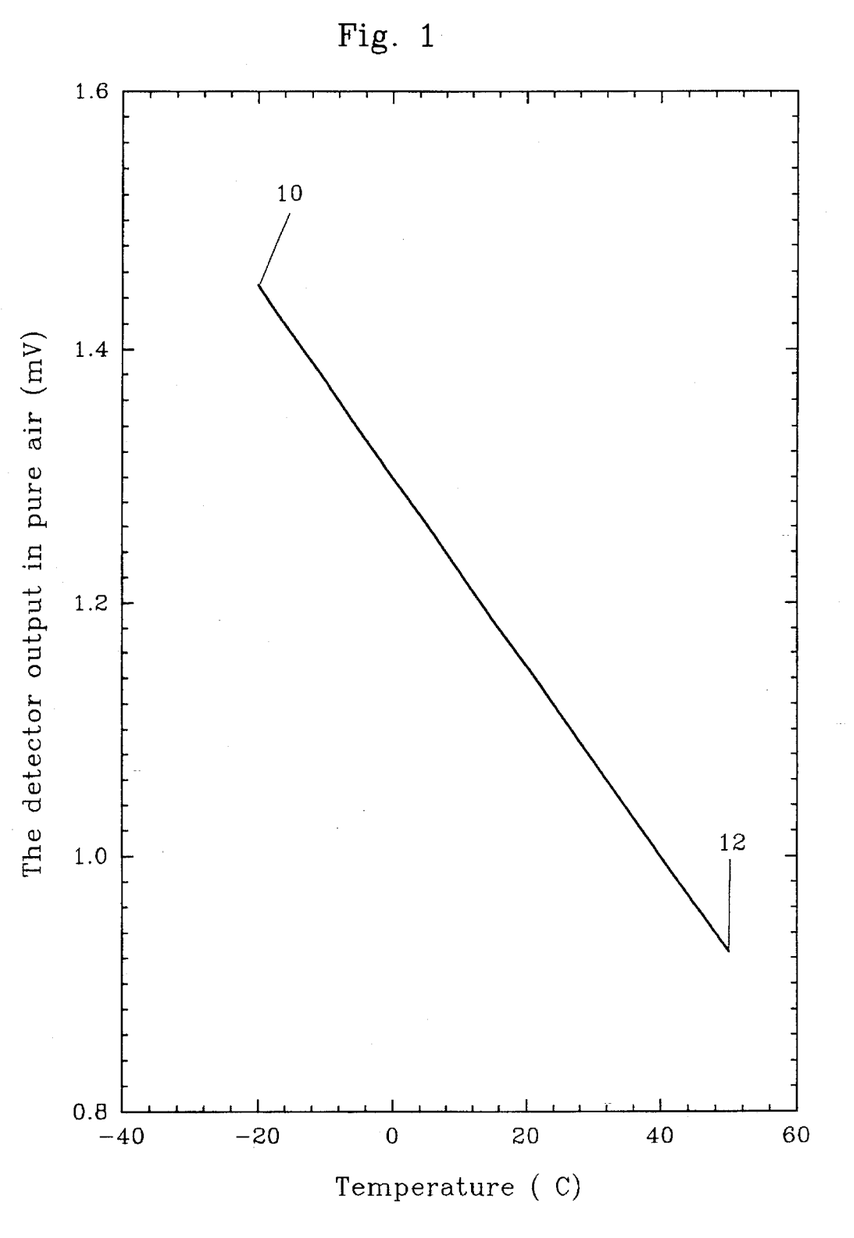
FIG. 1 is a graph of an output signal produced by a conventional gas analyzer wherein the sample chamber contains pure air at approximately −20° C. to approximately 50° C.

FIG. 1 illustrates the effect of an ambient temperature change on a conventional NDIR gas analyzer employed to determine the concentration of a gas. Pure air was introduced into the sample gas chamber of a conventional gas analyzer. The optical band pass filter provided in the conventional gas analyzer did not allow light having wavelengths in the absorption spectra of the gases contained in pure air to pass to the detector. Thus, no change in signal should be recorded. As can be seen in FIG. 1, the detector output signal decreased with an increase in ambient temperature. Specifically, the detector output signal decreased from approximately 1.45 mv at approximately −20° C. shown at 10 to approximately 0.95 mv at approximately 50° C. shown at 12. This decrease in output signal would normally indicate an increase in the concentration of the gas being detected and thus, absorbed. However, this was not the case. Hence, the conventional gas analyzer is not reliable when utilized to determine the concentration of a gas if a change in ambient temperature occurs.

Figure 2:
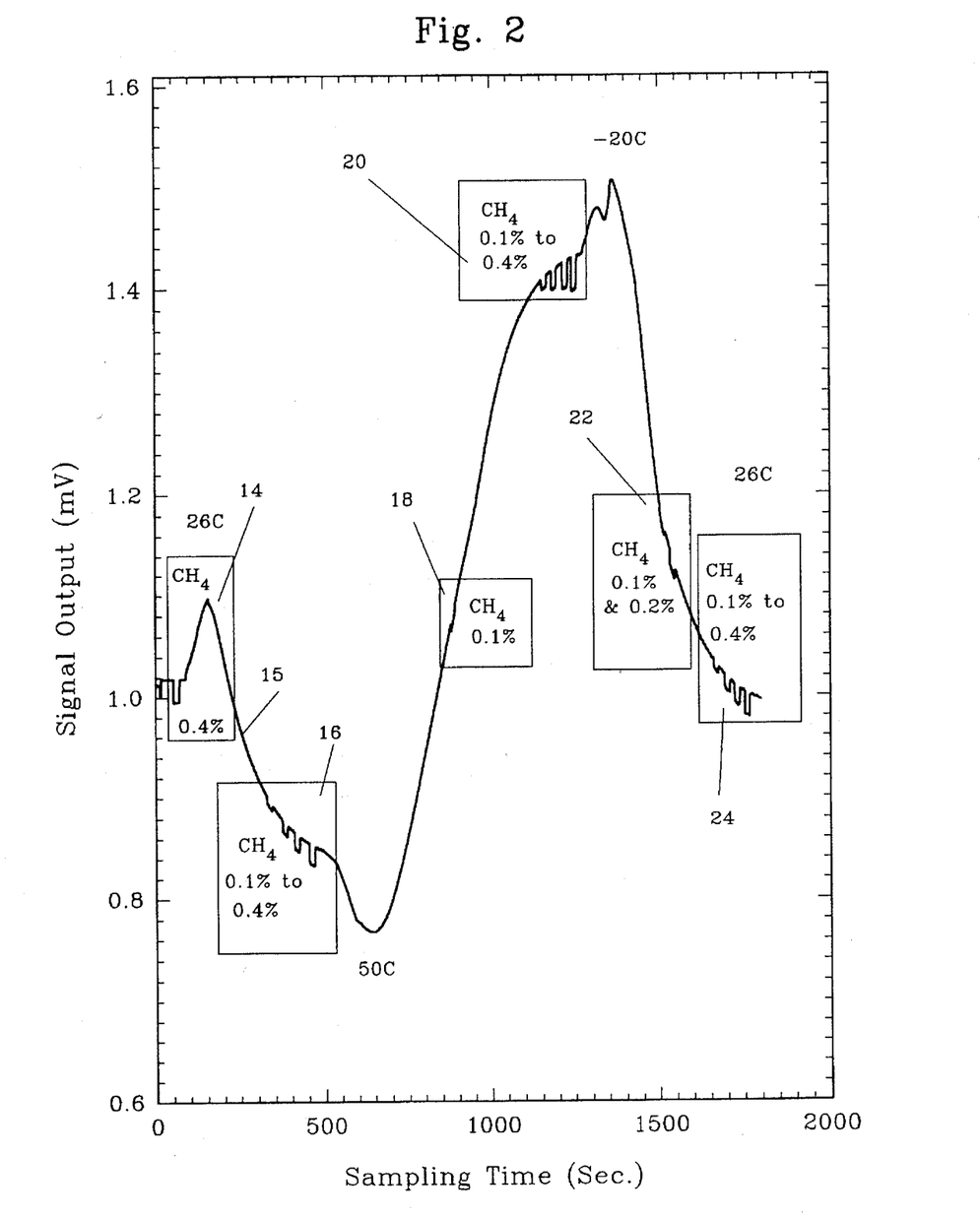
FIG. 2 is a graph of an output signal produced by a conventional gas analyzer wherein the sample chamber was filled and purged of sample gas mixtures containing between 0.1% to 0.4% methane at room temperature in which the temperatures over time and movement of the gas ranged from approximately 26° C. to 50° C. to −20° C. back to 26° C.

FIG. 2 is a graph which illustrates the conventional gas analyzer detector output signal in units of millivolts versus the sampling time in units of seconds. This data indicates that a conventional gas analyzer employed in determining the concentration of a known gas is insensitive to the introduction of relatively small concentrations of gas into the sample chamber if a change in ambient temperature occurs. At approximately 75 seconds and 26° C., a gas mixture containing 0.4% methane (4000 p.p.m.) was introduced into the sample chamber and the conventional gas analyzer responded with a small but noticeable change in the output signal of approximately a 0.025 mv. drop in the output signal at 14a. This sample gas mixture containing 0.4% methane was then purged from the sample chamber using pure air. With pure air filling the sample chamber, the ambient temperature changed from approximately 26° C. to approximately 50° C. and the output signal decreased, as shown at 15.

Once the 0.4% methane mixture was purged from the chamber using pure air, gas mixtures containing 0.1% (1000 p.p.m.), 0.2% (2000 p.p.m.), 0.3% (3000 p.p.m.), and 0.4% (4000 p.p.m.) methane were successively introduced and then purged from the chamber using pure air starting at approximately 275 seconds and approximately 50° C. The introduction of gas mixtures containing 0.1%, 0.2%, 0.3% and 0.4% methane resulted in a detector output signal shown at 16. The output signal illustrating the introduction of the mixtures containing 0.1% methane and 0.2% methane is almost undetectable at 16 because of the negative slope of the output signal resulting from the ambient temperature change from approximately 26° C. to approximately 50° C.

After purging the sample gas mixture containing 0.4% methane from the chamber using pure air, a mixture containing 0.1% methane was introduced into the chamber at approximately 900 seconds shown at 18. The detector output signal indicating the introduction of the 0.1% methane mixture into the chamber is hardly noticeable as a result of the relatively steep positive slope created by the change in ambient temperature from approximately 50° C. to approximately −20° C.

The changes in the output signal at 20 are almost imperceptible because of the steep positive slope created by the ambient temperature change from approximately 50° C. to approximately −20° C. Likewise, as the ambient temperature changed from approximately −20° C. to approximately 26° C. the introduction and purging of gas sample mixtures containing 0.1% and 0.2% methane starting at approximately 1500 seconds shown at 22 are hardly discernible when examining the detector output signal. Gas sample mixtures having 0.1%, 0.2%, 0.3% and 0.4% methane were successively introduced and purged from the sample gas chamber as shown at 24. The changes in the output signal which resulted at 24 were hardly noticeable. Further, because output signals shown in FIG. 2 are hardly noticeable concentration cannot be accurately measured from the graph.

DESCRIPTION OF RELATED ART

Some prior art gas analyzing devices attempt to compensate for the detrimental effects resulting from a change in ambient temperature by providing the conventional gas analyzer with a second reference chamber containing a known reference gas with a known gas concentration. Gas concentration data from both the sample chamber and the second reference chamber is collected and the data generated from the sample chamber is calibrated using the data generated from the second reference chamber in an attempt to eliminate the temperature effect. One example of this type of device is described in U.S. Pat. No. 4,937,448 to Mantz et al. A second reference chamber containing a known reference gas is positioned in longitudinal alignment with a sample chamber, a laser is passed through the two longitudinally aligned chambers and isotope measurements are taken. The isotope concentration of the sample gas is then determined by subtracting the known isotopic concentration of the known reference gas from the actual measured isotopic concentration.

Another type of gas analyzer which incorporates a second reference chamber is described in U.S. Pat. No. 4,157,470 to Kotaka et al. The gas analyzer comprises a sample chamber, a temperature compensation cell, a second reference chamber containing a known gas with a known concentration, and an interference cell. The sample chamber and the temperature compensation cell are positioned in longitudinal alignment such that light passes through both. Likewise, the second reference chamber and the interference cell are also positioned in longitudinal alignment such that light can passes through both the chamber and the cell. The output signal from the sample chamber is calibrated by utilizing the data from the interference cell, the second reference chamber and the temperature compensation cell. The drawback of a gas analyzer having a second reference chamber is that the physical characteristics of the sample chamber may not be identical to that of the second reference chamber. Hence, the output signal measured from the second reference chamber may cause an erroneous sample chamber output signal because the two chambers are not exposed to identical conditions.

Other prior art devices employ two detectors and two light beams to compensate for the inaccuracies of the conventional gas analyzer due to a change in ambient temperature. One detector is provided with a band pass filter that is sensitive to the absorption spectrum of the gas being detected. The second detector is provided with a second band pass filter that is sensitive to the background environment of the sample chamber. The output signal produced by the background detector is subtracted from the output signal produced by the detector sensing the gas being detected. The drawback of this type of device is that the physical characteristics of the sample chamber containing the two detectors may not be uniform. For example, the two detectors may respond to the same temperature change at different times. If the temperature change is not uniform throughout the chamber, the output signal will be erroneous. An example of this type of device is described in U.S. Pat. No. 5,013,920 to Asano et al.

Other prior art NDIR gas analyzers attempt to counter the detrimental effects of a change in ambient temperature by providing the gas analyzer with a temperature control element. This type of nondispersive gas analyzer is described in U.S. Pat. No. 5,163,332 to Wong. The temperature control element in Wong specifically is used to prevent the sample chamber from reaching a temperature above the dew point temperature in order to avoid condensation from forming on the sample chamber surface. The temperature control element is not designed to maintain the sample gas chamber at a uniform and constant temperature, but is designed to keep the sample chamber temperature above the dew point. Even slight changes in temperature can detrimentally affect the conventional gas analyzer. Further, if you were able to control the temperature such that any change in temperature would be prevented, the increase in the amount of electrical power and the increase in size of the gas analyzer necessary to maintain the temperature would substantially make using the device prohibitive.

Yet another type of prior art device provides a light source which is electronically pulsed between an on and off position such that the detector receives an interrupted stream of light creating an output signal which returns to baseline when the light source is in the off position. The drawback of this method is that the apparatus cannot differentiate between a change in electrical signal created by low frequency electrical noise and small changes in the output signal created by gas absorbing light. Noise can be created by lamp warm up and cool down or warm up due to long thermal time constants of the thermopile. An example of this type of device is disclosed in U.S. Pat. No. 4,709,150 to Burough et al.

There is a need for a method and an apparatus which are able to determine the concentration of a known gas and which are insensitive to a change in the ambient temperature.

SUMMARY OF THE INVENTION

I provide a method and apparatus for determining the concentration of a known gas in a sample gas mixture which is insensitive to a change in the ambient temperature. The method substantially comprises the steps of providing light through a chamber, introducing the sample gas mixture into the chamber, detecting the light in the chamber, producing an electric output signal, measuring the output signal for a plurality of instantaneous time periods, calculating the change of the output signal (CS), calculating the change of the change of the output signal (CCS) and comparing the CCS data with corresponding CCS data for the known gas with a known concentration at a range of known temperatures.

I further provide that the method utilizing CCS may include repeatedly switching on and off the light source, creating interrupted light through the chamber and detecting the light when the light is present in the sample chamber and when the light is absent in the sample chamber. This technique establishes a zero baseline from which all light sensed by the detector can be measured.

In accordance with another aspect of my method for determining the concentration of a known gas, I provide that the step of detecting the light may include providing a second reference sealed chamber containing a known gas having a known concentration and alternatively detecting the amount of light in the sample chamber and the amount of light in the second reference chamber.

Yet another aspect, of my method for determining the concentration of a known gas is providing that the step of producing an electric output signal can include providing a database having CCS data generated from a known gas with a known concentration at a known temperature range and alternately accessing the CCS data from the database and the CCS data generated from the sample chamber.

I further provide several manners in which the CCS data can be compared. One way of comparing the CCS data is to compare the peak values of the CCS data generated from the sample chamber with the peak values of CCS data of the same gas having a known concentration at a known range of temperatures provided by a pre-existing database.

Another way of comparing the CCS data is to compare the summation of the absolute values of the CCS data generated from the sample chamber to the summation of the absolute values of CCS data of the same gas having a known concentration at a known range of temperatures provided by a pre-existing database.

Yet another manner in which to compare the CCS data is to compare a summation of CCS data generated from the sample chamber multiplied by the corresponding time interval to the summation of the CCS data multiplied by the corresponding time interval. The latter CCS data is provided by a pre-existing database having CCS data for the same gas at known concentrations and at known range of temperatures.

I further provide an apparatus to perform my method of determining the concentration of a known gas in a sample gas mixture. The apparatus substantially comprises a sample gas chamber, an infrared light source, a detector positioned in the chamber, a signal converter, and a data acquisition and microprocessor unit for measuring the output signal at a plurality of instantaneous time periods. The data acquisition and microprocessor unit has a memory with a program that can calculates both the change of the output signal (CS) and the change of the change of the output signal (CCS).

Yet another aspect of my apparatus for determining the concentration of a known gas is to provide a narrow optical band pass filter positioned in front of the detector allowing only light having wavelengths specific to the absorption spectrum of the gas being detected to pass therethrough thus, filtering out all other wavelengths.

I further provide my data acquisition and microprocessor unit with a database containing output signals and CCS data for concentrations of known gases at a range of known temperatures. The database specifically includes peak values of CCS data, a summation of the absolute values of the CCS data and a summation of CCS data multiplied by its corresponding time interval.

BRIEF DESCRIPTION OF DRAWINGS

FIG. 5b is a graph of the change of the signal output (CS) shown in FIG. 5a.

FIG. 5c is a graph of the change of the change of the signal output (CCS) shown in FIG. 5a.

DETAILED DESCRIPTION OF THE PREFERRED EMBODIMENT

Figure 3:
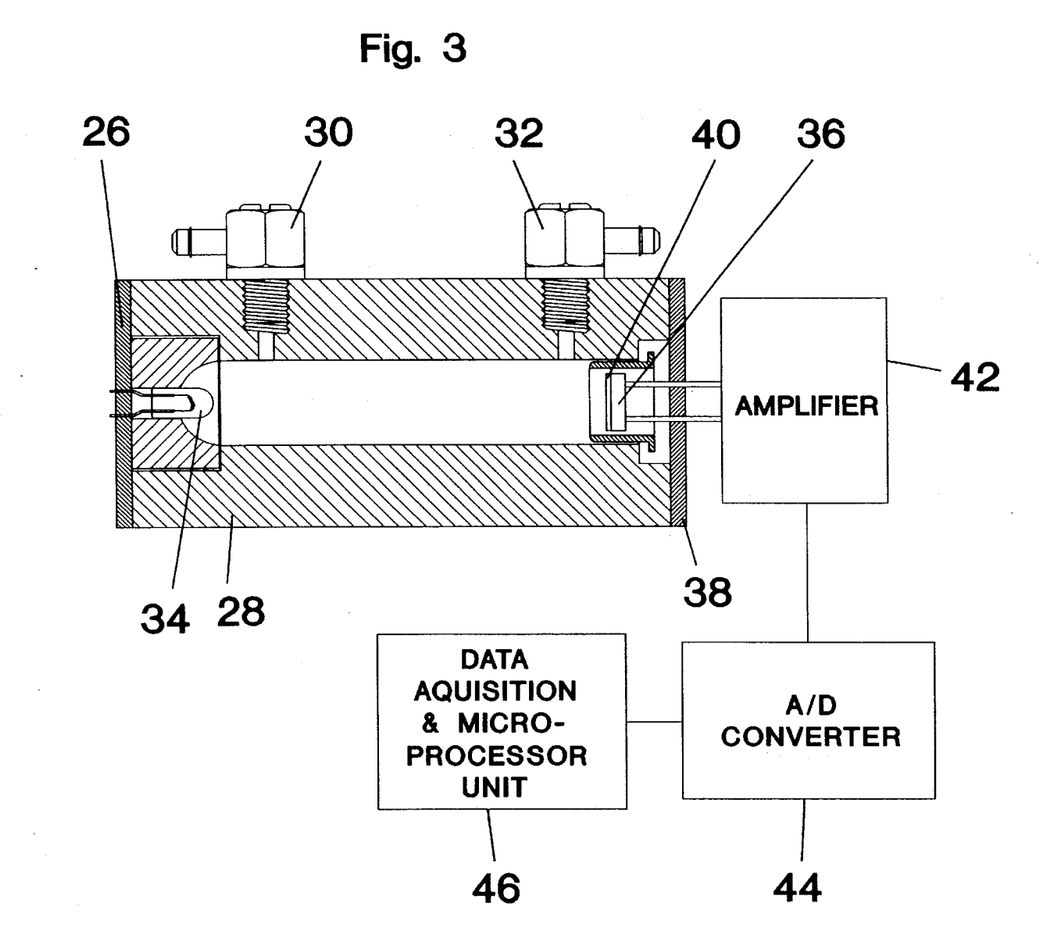
FIG. 3 is a schematic of my gas analyzer apparatus for determining the concentration of a known gas in a sample mixture.

As shown in FIG. 3, a presently preferred embodiment of my gas analyzer 26 substantially comprises a sample gas chamber 28 having an inlet 30 and an outlet 32, an infrared light source 34, a detector 36 connected to a circuit board 38, an optical band pass filter 40, an amplifier 42, an analog to digital (A/D) converter 44, and a data acquisition and microprocessor unit 46. Infrared light source 34 and detector 36 are both positioned within the sample gas chamber 28 wherein infrared light source 34 is able to be connected to a power source (not shown). Infrared light source 34 can be an incandescent lamp, as well as a laser, a ceramic infrared radiator or a light emitting diode. Detector 36 is preferably a thermopile but could also be a pyroelectric infrared detector or a semiconductor infrared detector. Detector 36 is mounted on circuit board 38. I have found that the following commercially available components can be used:

| Component | Component No. | Source | Ref. No. |
| --- | --- | --- | --- |
| Light Source | 133 | Carley | 34 |
| Detector | 2M | Dexter | 36 |
| Data Acquisition & Microprocessor Unit | PC Lab Plus Plus | National Instrument | 46 |

In operation, light source 34 is turned on, providing light through sample gas chamber 28. A sample gas mixture (not shown) is then introduced into sample chamber 28 through inlet 30. Because the gas being detected within the sample mixture is known, the wavelength absorption spectrum of the gas is known. Hence, detector 36 is provided with an optical band pass filter 40 which will only pass wavelengths that are absorbed by the gas being detected and will filter out other wavelengths. Once detector 36 has sensed the light within sample chamber 28, circuit board 38 will create an electrical output signal which is a function of the light detected. The electrical output signal is then entered into amplifier 42. After amplification of the output signal, the output signal is then converted from an analog signal to a digital signal by A/D converter 44. The amplified digital output signal is then entered into data acquisition and microprocessor unit 46. Data acquisition and microprocessor unit 46 is provided with a memory having a program which calculates CS data, CCS data, a summation of the peak values of the CCS data, and a summation of the CCS values multiplied by the time interval. Data acquisition and microprocessor unit 46 can also generate a plot of all of the calculated data as well as a plot of the digital output signal. Although data acquisition and microprocessor unit 46 is illustrated as one unit, two devices can be implemented in place of unit 46. For example, one device could transfer the output signal from the A/D converter 44 to a second device being a microprocessor having a memory able to calculate the CCS data.

Figure 4:
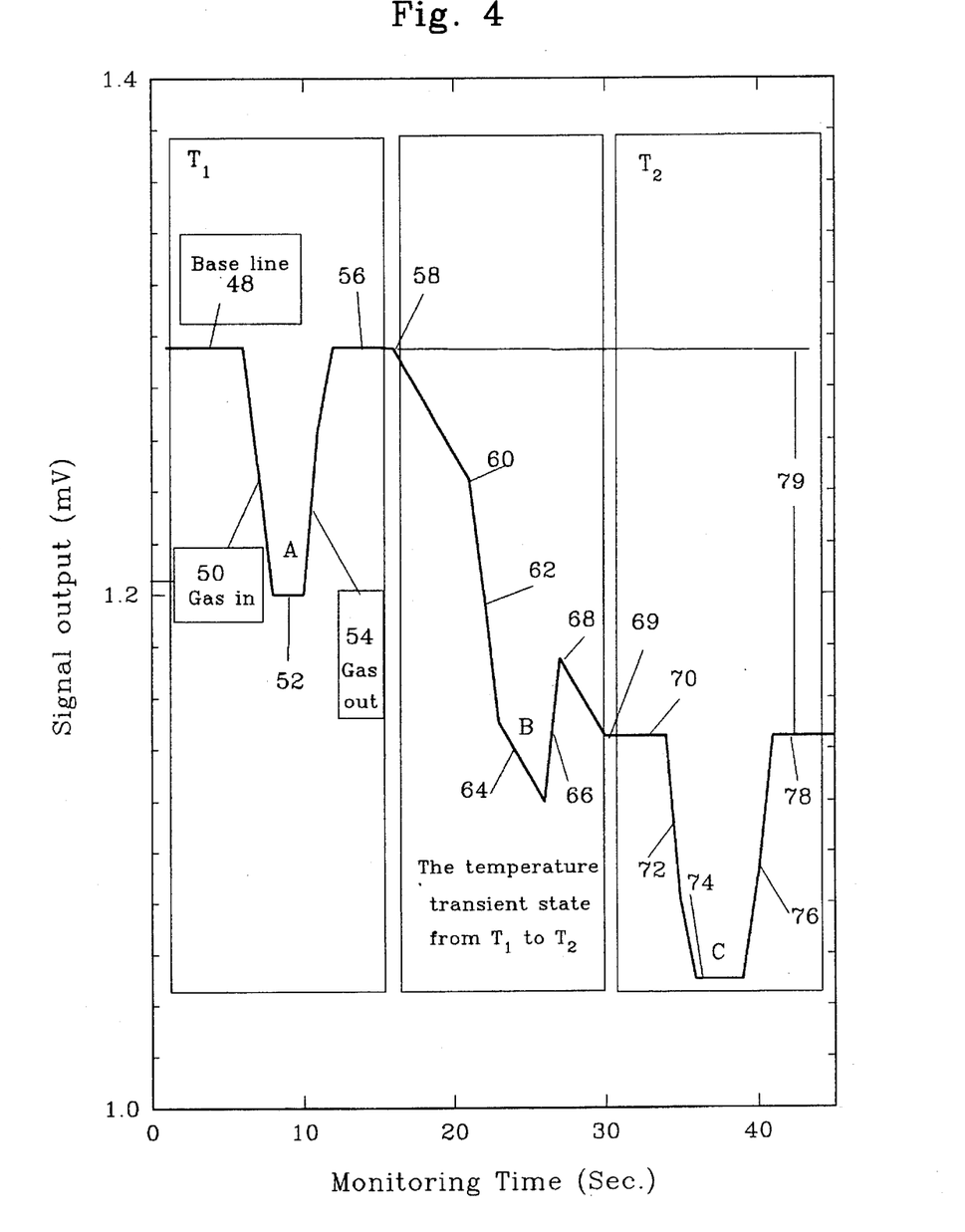
FIG. 4 is a graph of an output signal obtained using my gas analyzer apparatus shown in FIG. 3.
Figure 5A:
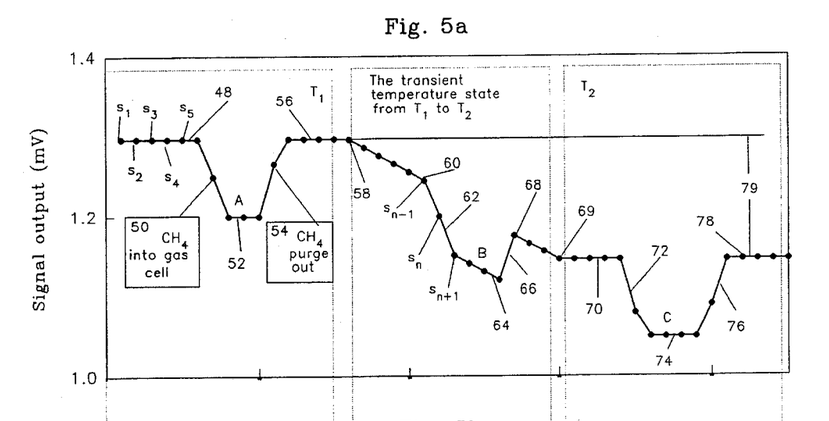
FIG. 5a is the same output signal shown in FIG. 4 illustrating the digital output signal.

FIGS. 4, 5a, 5b and 5c, illustrate graphs generated by data acquisition and microprocessor unit 46 when a sample gas mixture containing methane was repeatedly introduced and purged from sample gas chamber 28 of my gas analyzer 26. Referring specifically to FIGS. 4 and 5a which both illustrate substantially the same data, it can be seen that the ambient temperature change from $T_1$ to $T_2$ adversely affects the reliability of the output signal. Initially, there is air within sample gas chamber 28 which is indicated by a baseline signal at 48 equal to approximately 1.3 mv. As the sample gas mixture is introduced into sample gas chamber 28, the output signal responded with a negative slope at 50 indicating that the gas within sample gas chamber 28 absorbed the light at a wavelength within the spectrum selected by optical band pass filter 40. When all of the air was substantially purged from the sample gas chamber 28 and the sample gas mixture substantially filled the sample chamber 28, a constant output signal equal to approximately 1.2 mv was indicated by the output signal at 52. As the sample gas mixture was purged from sample gas chamber 28, the output signal exhibited a positive slope at 54 until the output signal returned to a baseline output signal at 56. The baseline output signal was constant and equal to approximately 1.3 mv at 56 which indicates that the gas within sample gas chamber 28 was substantially all air. As can be seen, the air did not absorb the light within sample gas chamber 28 at the wavelength specified by band pass filter 40.

Although the air within the sample gas chamber remained the same as the ambient temperature changed from $T_1$ to a transient state, the baseline shifted starting at 58 and continuing to 60. At a monitoring time of approximately 20 seconds, the same sample gas mixture that was previously introduced was again introduced into sample gas chamber 28 at 60 and the air was purged from sample gas chamber 28 for a second time. This is indicated by the negative slope at 62. When substantially all of the air was purged from the sample gas chamber 28 and the sample gas mixture substantially filled the sample chamber 28, the output signal exhibited a change in slope at 64. Because the ambient temperature was constantly changing in the transient state, the output signal did not reach a constant when all of the air was purged and the sample gas chamber 28 was substantially filled with the sample gas mixture as was the case during the previous introduction of the sample gas mixture into the sample gas chamber 28 shown at 52. The constantly changing temperature created a negative slope in the output signal at 64. The sample gas mixture was then purged from the sample gas chamber 28 as is indicated by the positive slope of the output signal at 66. When the sample gas chamber 28 was filled again with substantially all air, the output signal exhibited a baseline having a negative slope starting at 68 and continuing until the temperature reached $T_2$ at 69. The baseline at 68 through 69 has a negative slope resulting from the ambient temperature constantly changing in the transient state.

Although the air within the sample gas chamber 28 remained the same during the ambient temperature change from the transient temperature state to $T_2$, the baseline underwent a shift as seen when comparing the output signal at 68 through 69 with 70. The introduction of the sample gas mixture containing methane into the sample gas chamber 28 for the third time resulted in the output signal having a negative slope at 72. When substantially all of the air was purged and the sample gas chamber 28 was substantially filled with the sample gas mixture, the output signal exhibited a constant signal equal to approximately 1.05 mv at 74. When the sample gas mixture was purged from sample gas chamber 28, the output signal took the form of a positive slope at 76. After substantially all of the sample gas was purged from sample gas chamber 28 and sample gas chamber 28 contained substantially all air, the output signal returned to a baseline equal to approximately 1.14 mv at 78.

This experiment further illustrates the inaccuracy of the conventional gas analyzer when determining the concentration of gas during an ambient change in temperature. Although the concentration of the gas being detected remained substantially the same during the three times the sample gas mixture was introduced and purged from sample gas chamber 28, the output signal which is inversely proportional to the gas concentration exhibited a considerable change between the first introduction of the sample gas mixture at 52 and the third introduction of the sample gas mixture at 74. This change can be seen by examining the baseline drift 79.

When the output signal was obtained, the A/D converter 44 transformed the output signal shown in FIG. 4 to the digital signal output, S, shown in FIG. 5a. The digital signal output, S, was then utilized by data acquisition and microprocessor unit 46 to calculate the change of the signal (CS).

Figure 5B:
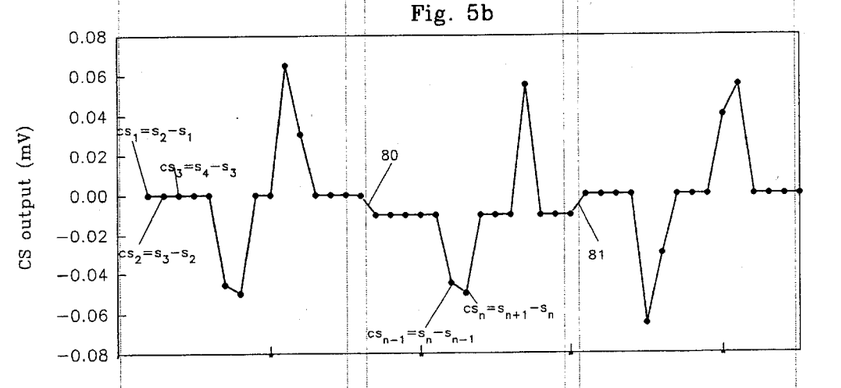

FIG. 5b illustrates the change of the output signal (CS). In order to produce the graph of FIG. 5b sample output signal points $S_1, S_2, S_3, S_4, \ldots, S_{n-1}, S_n, S_{n+1} \ldots$ were measured and used to calculate CS. $CS_1$ is equal to the second output signal minus the first output signal, i.e., $CS_1=S_2-S_1$. In general, CS is calculated as the present output signal minus the previous one, i.e, $CS_{n-1}=S_n-S_{n-1}$. $CS_{n-1}$ could also be calculated as the relative difference between $S_n$ and $S_{n-1}$. Compared to baseline drift 79 illustrated in FIGS. 4 and 5a, the baseline drift shown in FIG. 5b is relatively small although a small drift can be detected at the transient temperature state between $T_1$ and $T_2$ at 80 and 81, respectively.

Figure 5C:
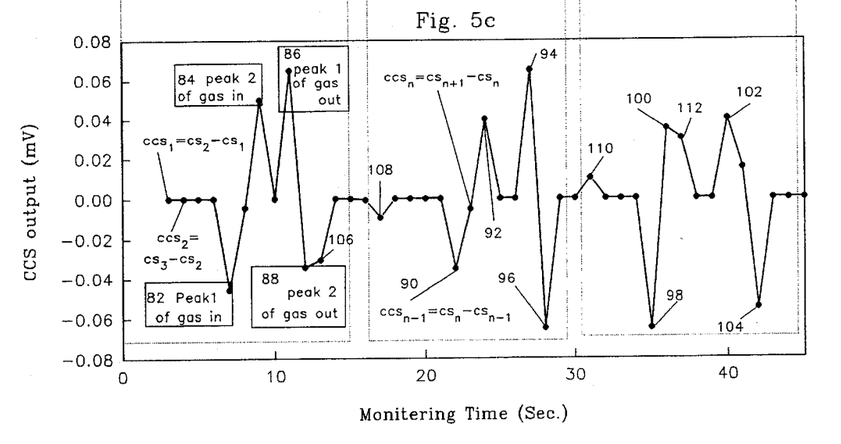

FIG. 5c illustrates the change of the change of the signal (CCS). CCS is calculated as $CCS_1=CS_2-CS_1$ and more generally as $CCS_{n-1}=CS_n-CS_{n-1}$ which is equivalent to the second derivative of the output signal where $\Delta t=1$. CCS data can alternatively be calculated by determining the relative difference between $CS_n$ and $CS_{n-1}$ which can then be used when comparing the CCS data to determine the concentration of the gas in the sample mixture. The CCS equation is based on the theory that the concentration of gas being detected and the light being absorbed by the gas exhibits a linear relationship which is specifically expressed by Beer-Lambert Law which is:

$$I=I_0 exp(-\alpha x) \tag{1}$$

where I is the transmitted light intensity which in this case is the output signal; $I_0$ is the incident light intensity; $\alpha$ is the absorption coefficient; and x is the optical path through the absorbent. Here, $\alpha$ is directly related to the type of gas and the concentration of the gas. The higher the concentration, the larger $\alpha$. Equation 1 is a linear equation which can generally be expressed as:

$$y=f(t) \tag{2}$$

where y is a function of time, t. The first derivative is:

$$\frac{dy}{dt} = \lim_{\Delta t \to 0} \left( \frac{\Delta y}{\Delta t} \right) \simeq \frac{y_2 - y_1}{t_2 - t_1} \qquad (3)$$

where $$\Delta y = y_2 - y_1, \qquad (4)$$

$\Delta y$ is the change of the signal, and $$\Delta t = t_2 - t_1 \qquad (5)$$

thus, $$\frac{d^2 y}{dt^2} = \frac{d(dy/dt)}{dt} \simeq \frac{(\Delta y/\Delta t)_2 - (\Delta y/\Delta t)_1}{t_2 - t_1}. \qquad (6)$$

In this case $\Delta t = 1$, thus:

$$\frac{d^2 y}{dt^2} \simeq \Delta y_2 - \Delta y_1 \qquad (7)$$

which is the change of the change of the signal (CCS), i.e., $CCS_{n-1} = CS_n - CS_{n-1}$. The baseline drift 79 in FIG. 5a is substantially eliminated in the CCS data shown in FIG. 5c even within the transient temperature state. The introduction of a gas sample mixture into sample gas chamber 28 can be identified by a negative peak followed by a positive peak illustrated for example, by digital output signals at 82, 84 and 90, 92 and 98, 100, 112 in FIG. 5c. Further, purging of a gas sample mixture from sample gas chamber 28 can be identified by a positive peak followed by a negative peak illustrated for example, by digital output signals 86, 88, 106 and 94, 96 and 102, 104 in FIG. 5c. CCS data at 108 and 110 and do not exhibit either pattern and therefore would not be considered in comparing the CCS data.

Figure 6:
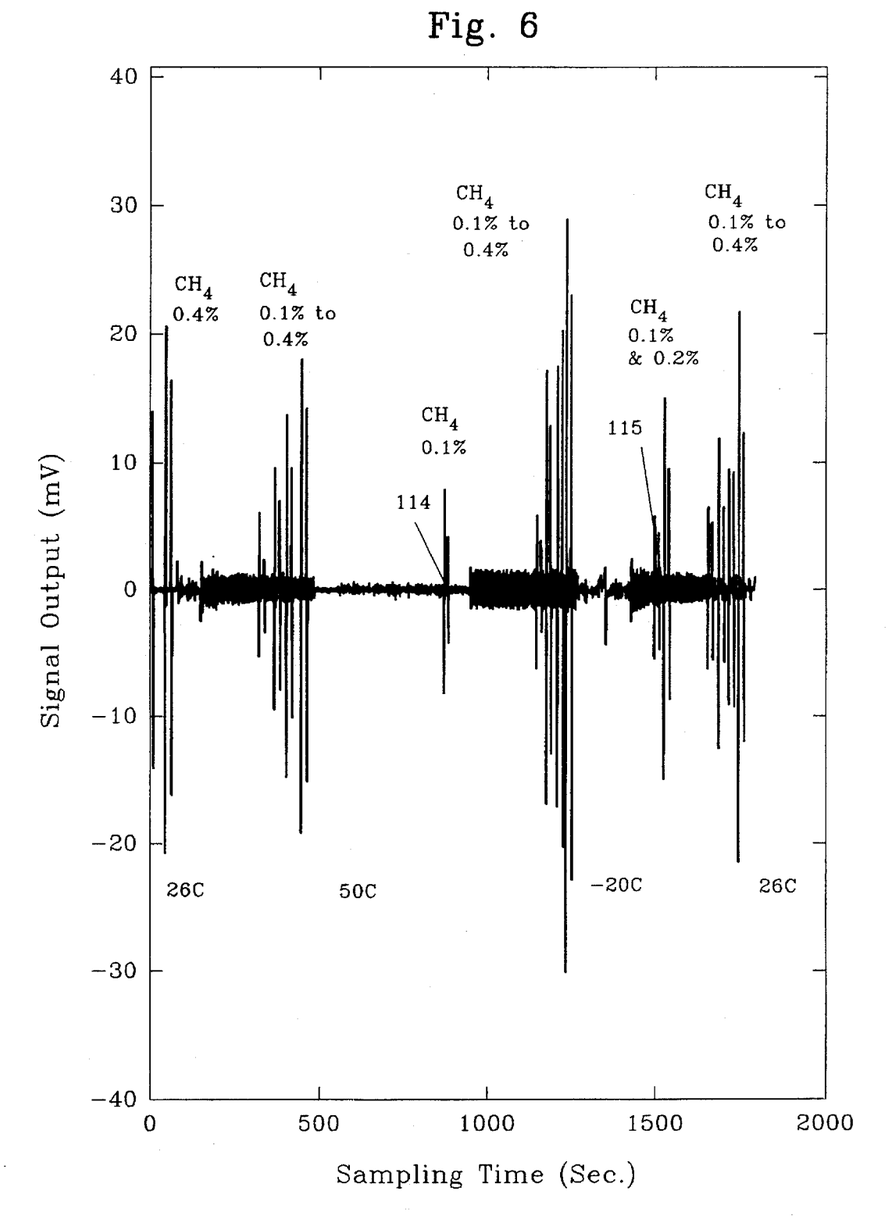
FIG. 6 is a graph of CCS data developed using my method and apparatus for determining gas concentration wherein the sample gas chamber was filled and purged of sample gas mixtures containing between 0.1% to 0.4% methane similar to that shown in FIG. 2.

FIG. 6 illustrates CCS data which was obtained when sample gas mixtures containing methane concentrations between 0.1% to 0.4% were introduced into sample chamber 28 in a pattern substantially the same as that discussed when previously referring to FIG. 2. The CCS data in FIG. 2 was obtained using a conventional gas analyzer and method. Comparing the output signal of FIG. 2 to CCS data of FIG. 6, one can see that the CCS method virtually eliminates baseline shift. As noted above when discussing FIG. 2, detection of gas sample mixture containing 0.1% and 0.2% methane shown at 14, 16, 18, 20, 22, 24 are almost not noticeable. However, referring to FIG. 6, CCS data signal corresponding to sample gas mixtures containing 0.1% and 0.2% methane being introduced into sample gas chamber 28 are quite noticeable. Specifically, FIG. 2 at 18 and 22 represent the introduction of sample gas mixtures containing 0.1% and 0.2% methane into chamber 28. Turning to FIG. 6 at 114 and 115, sample gas mixtures containing 0.1% and 0.2% methane were introduced into sample chamber 28 and are quite noticeable.

After calculating the CCS data, various comparison techniques can be utilized which compare the CCS data generated using my gas analyzer to CCS data from a pre-existing database for the gas being detected. The pre-existing CCS database can be created by compiling CCS data for a certain gas at several temperatures and at several concentrations.

Figure 7:
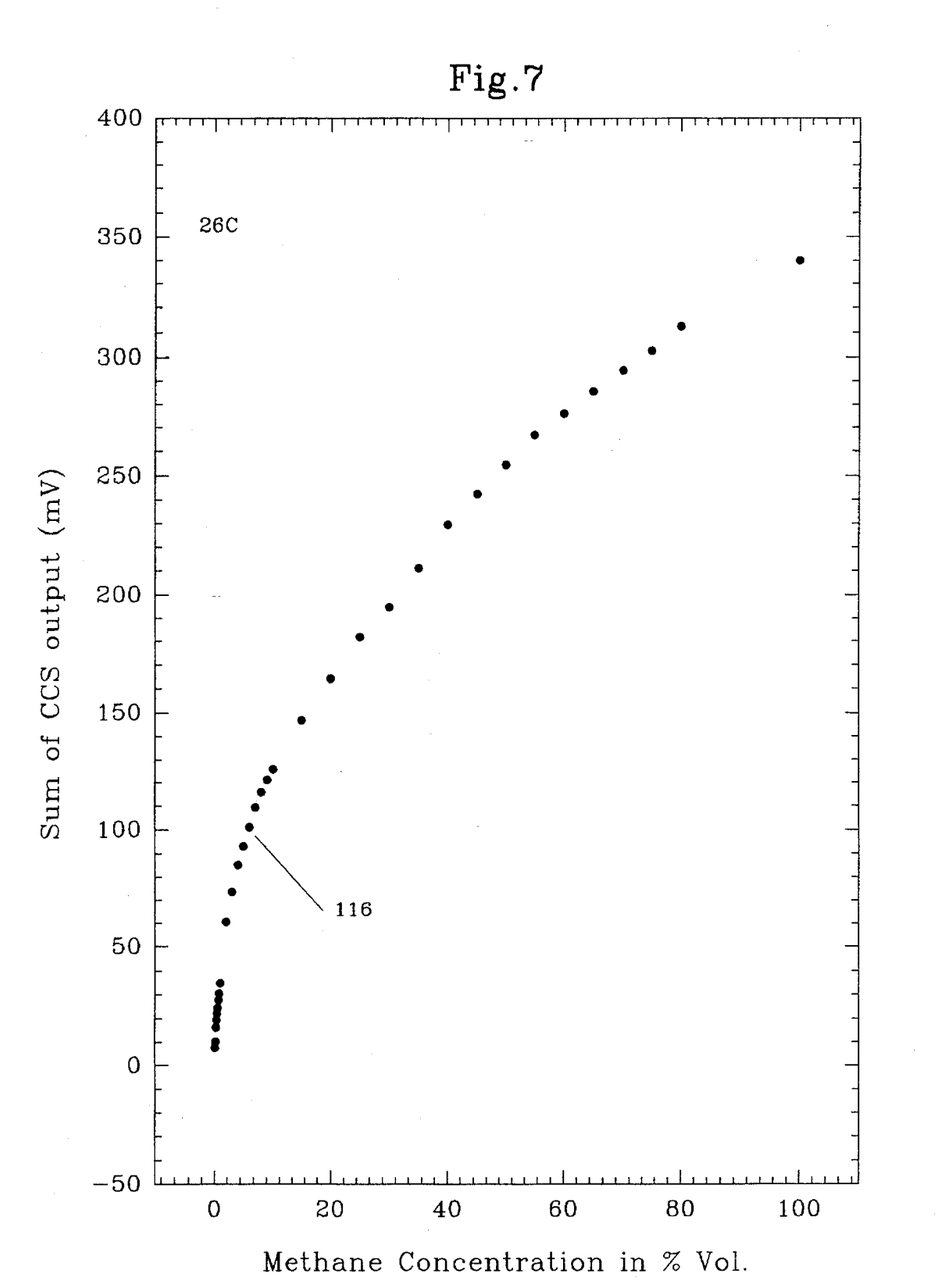
FIG. 7 is a graph of a methane response curve developed using my method and apparatus for determining gas concentration.

FIG. 7 illustrates a response curve for concentration of methane between 0% and 100% developed using my CCS method and apparatus. The response curve was created by summing all the CCS values and plotting the sum CCS values on the graph. Each charted point on the graph represents a specific concentration of methane at approximately 26° C. This data can be utilized in future determinations of methane concentration using my CCS method. After CCS data generated from sample chamber 28 is calculated in the field, the summation of the CCS data can be compared with the data on the response curve to find the specific gas concentration. For example, if the summation of the CCS values generated on site was 100 mv, referring to FIG. 7, the corresponding concentration would be approximately 7% methane as shown at 116. By entering the response curve shown in FIG. 7 into a database in data acquisition and microprocessor unit 46, the new data taken on site can be compared with this pre-existing database and the concentration of methane in a gas sample mixture could be determined. A temperature probe (not shown) would have to be provided in my presently preferred embodiment of my gas analyzer shown in FIG. 3.

Although other manners of comparison can be utilized with the CCS data, three presently preferred comparison techniques which follow can be utilized. First, one could compare the peak values of the CCS data to the database CCS peak values to determine the concentration of the gas being detected. For example, referring to FIG. 5c, CCS peak values at 82, 84, 90, 92, 98 and 100 could be compared to the CCS peak values in the stored database. The concentration of the gas being detected is determined by substantially matching the CCS peak values with the database CCS peak value of the same gas at a known concentration.

The baseline shift illustrated at 58 through 60 and at 68 through 69 in FIG. 5a results in small peaks at 108 and 110, respectively, in FIG. 5c. Because small peaks 108 and 110 are not part of a pattern of a sample gas mixture either being introduced or purged from the chamber, these small peaks 108, 110 should not be considered when determining the concentration of the gas. One way these type of small peaks could be eliminated from the CCS data which is compared to determine the gas concentration is to program data acquisition and microprocessor unit 46 to only consider CCS data in a pattern which indicates an introduction of sample gas mixture into the chamber, i.e., a negative peak followed by a positive peak. Also, a predetermined minimum absolute peak value could be chosen by the user such that any peak value of the CCS data less than the predetermined minimum absolute value would not be used in the comparison of the CCS data. This would eliminate any data created by electrical noise from being compared.

Second, one could compare the summation of the absolute values of the CCS data generated using my presently preferred method and apparatus to the summation of the absolute value of each CCS values in the pre-existing CCS database. For example, the program could first establish when the gas is introduced into the sample chamber 28 and then purged from the sample gas chamber. Referring to FIG. 5c, the introduction of the gas into the sample gas chamber is illustrated at 82, 84 and purging of the gas from the gas chamber is illustrated at 86, 88. The program would then sum the absolute values of the CCS data between and including 82 and 84, then compare this summation to that CCS data of the pre-existing database and find the gas concentration having substantially the same CCS data.

Third, one could also compare the summation of each of the CCS values multiplied by the corresponding time interval to that of the pre-existing CCS database for the gas being detected at a variety of gas concentrations and at a range of temperatures. The gas concentration is proportional to the summation of each CCS value multiplied by the corresponding time interval. Each of the three techniques is easily implemented by a microprocessor program.

Because the CCS method is sensitive to rapid changes of the output signal, slow changes in concentration could go undetected. To avoid this, the presently preferred method can be adapted in the three following manners. One technique is to interrupt the light within sample chamber 28 by repeatedly switching light source 34 on and off and detecting light within sample gas chamber 28 both when light is present within sample chamber 28 and when light is absent in sample gas chamber 28. By repeatedly switching the light source 34 on and off while detecting the light in the sample chamber 28 slow changes can be more easily perceived in the output signal when using my method and apparatus. The light will be detected when light source 34 is on and there is light present in sample chamber 28 and when light source 34 is off, and light is absent in sample chamber 28. When the light is detected and the light source is off, the output signal will be zero which will create a zero reference for every CCS data corresponding to the light detected when the light is present in sample chamber 28.

Figure 8:
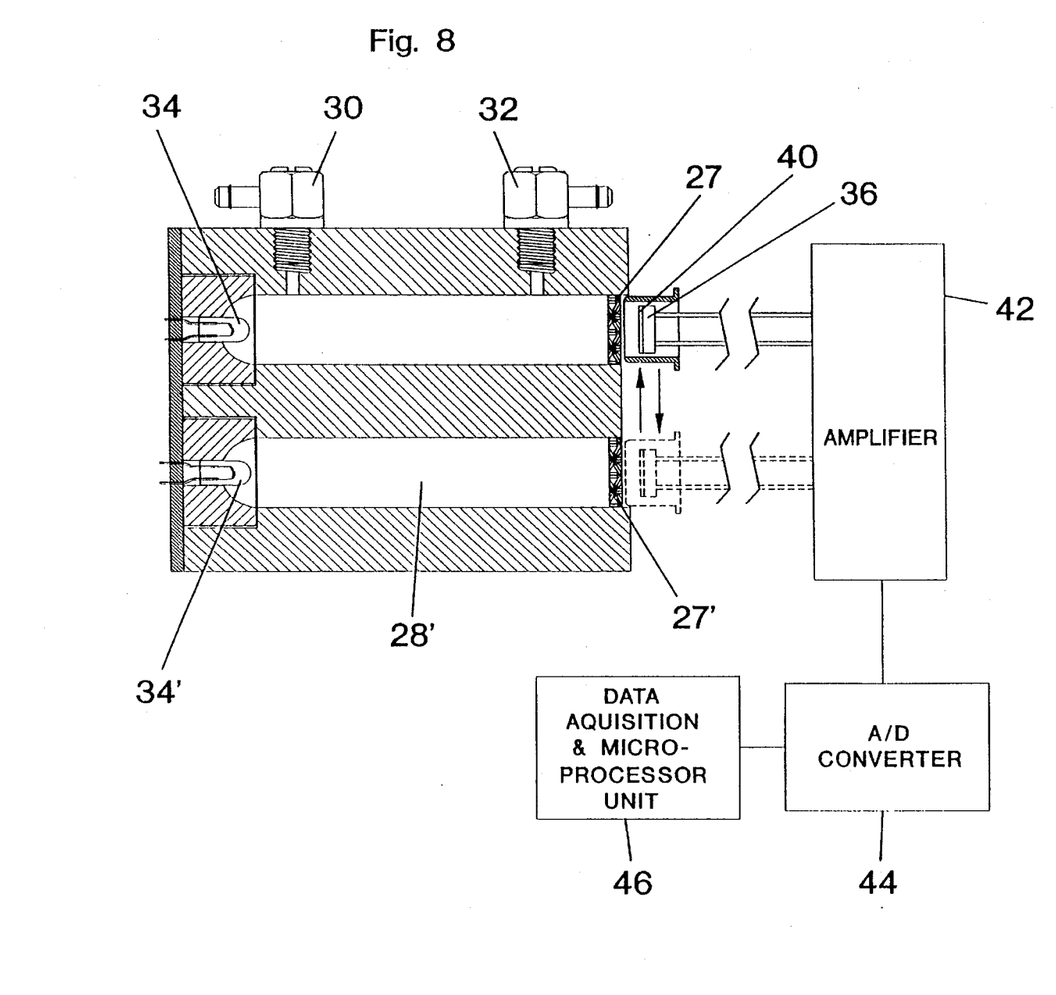
FIG. 8 is a schematic of another embodiment of my gas analyzer apparatus as shown in FIG. 3 showing a dual chamber gas analyzer apparatus for determining the concentration of a known gas in a sample mixture for providing a fixed reference output signal.

Another technique which will increase sensitivity of my presently preferred method and apparatus to slow changes in concentration is to alternate a second reference chamber 28' shown in FIG. 8 containing a known gas with a known concentration in the path of the light such that detector 36 alternatively senses the light within sample chamber immediately above the second reference chamber 28' and the light within the second reference chamber 28' containing the reference gas. For example, the second reference chamber 28' could contain pure air. An optical band pass filter would be provided which would prevent any light having wavelength in the absorption spectra of the gases present in air from passing to the detector. The detector 36 alternatively aligns to both the gas sample chamber and the second reference chamber 28'. Windows 27 and 27' sealed both the gas chambers with the corresponding light source 34 and 34' within the gas chambers. Hence, each time the light in the second reference 28' chamber was detected the output signal would be equal to zero creating a zero reference between each output signal corresponding to the light detected in the sample chamber.

Yet another technique that can be adapted to my presently preferred method and apparatus to make them more sensitive to slow changes in gas concentration is to obtain a database which includes CCS data generated using my gas analyzer having a known gas with a known concentration at a known temperature range in the sample chamber. For example, the temperature response curve for pure air for a known range of temperature as shown in FIG. 1 can be utilized. By alternatively plotting the CCS data generated using my method and apparatus and the pre-existing CCS data from the pure air response curve, slow changes in concentration could more easily be identified.

As described above, my method and apparatus are utilized to eliminate the detrimental effects of ambient temperature change on the conventional gas analyzer. Although not described my method and apparatus can be utilized to eliminate the detrimental effects of changes in temperature caused by any means.

My presently preferred method and apparatus have been described determining the concentration of methane. They can also be used for determining concentration for other gases such as carbon dioxide, carbon monoxide, nitrogen oxide and any other gas that has an infrared absorption spectrum. Also, my method and apparatus are applicable to chemicals in the liquid state and solid state where the chemicals have an infrared absorption finger print spectrum.

I claim:

1. A method for determining the concentration of a known type gas present in a gas sample mixture comprising:
   (a) providing light through a chamber;
   (b) introducing the gas sample mixture into the chamber;
   (c) detecting light in the chamber and producing an electric output signal which is a function of the amount of light detected;
   (d) measuring the output signal for three sequential instantaneous periods of time $t_1$, $t_2$, $t_3$;
   (e) determining the relative difference between the output signals at $t_1$ and the output signal at $t_2$ which gives a change of output signal value $CS_1$;
   (f) determining the relative difference between the output signal at $t_2$ and the output signal at $t_3$ which gives a change of output signal value $CS_2$;
   (g) determining the relative difference between the change of output signal value $CS_1$ and the change of output signal value $CS_2$ which gives a change of the change of the output signal value $CCS_1$;
   (h) repeating the method steps of (d) through (g) to develop a plurality of CCS data which generates a pattern; and
   (i) comparing the CCS data of step (h) to corresponding CCS data for the known type of gas at a range of known concentrations and at a range of known temperatures to determine the concentration of the known type gas in the sample mixture contained in the chamber.

2. A method for determining the concentration of a known type gas present in a gas sample mixture comprising:
   (a) providing light through a chamber;
   (b) introducing the gas sample mixture into the chamber;
   (c) detecting light in the chamber and producing an electric output signal which is a function of the amount of light detected;
   (d) measuring the output signal for four sequential instantaneous periods of time $t_1$, $t_2$, $t_3$, $t_4$;
   (e) determining the relative difference between the output signals at $t_1$ and the output signal at $t_2$ which gives a change of output signal value $CS_1$;
   (f) determining the relative difference between the output signal at $t_3$ and the output signal at $t_4$ which gives a change of output signal value $CS_2$;
   (g) determining the relative difference between the change of output signal value $CS_1$ and the change of output signal value $CS_2$ which gives a change of the change of the output signal value $CCS_1$;
   (h) repeating the method steps of (d) through (g) to develop a plurality of CCS data which generates a pattern; and
   (i) comparing the CCS data of step (h) to corresponding CCS data for the known type of gas at a range of known concentrations and at a range of known temperatures to determine the concentration of the known type gas in the sample mixture contained in the chamber.

3. A method for determining the concentration of a known type gas present in a gas sample mixture comprising:
   (a) providing light through a chamber;
   (b) introducing the gas sample mixture into the chamber;
   (c) detecting light in the chamber and producing an electric output signal which is a function of the amount of light detected;
   (d) measuring the output signal for a first instantaneous period of time $t_1$;
   (e) measuring the output signal for a second sequential instantaneous period of time $t_2$;

(f) measuring the output signal for a third sequential instantaneous period of time $t_3$;

(g) subtracting the output signal at $t_2$ from the output signal at $t_1$ which gives a change of signal value $CS_1$;

(h) subtracting the output signal at $t_3$ from the output signal at $t_2$ which gives a change of signal value $CS_2$;

(i) subtracting the value $CS_2$ from the value $CS_1$ which gives the change of the change of the signal value $CCS_1$;

(j) repeating the method steps of (d) through (i) to develop a plurality of CCS data which generates a pattern; and (k) comparing the CCS data of step (j) to corresponding CCS data for the known type of gas at a range of known concentrations and at a range of known temperatures to determine the concentration of the known type gas in the sample mixture contained in the chamber.

4. The method as recited in claim 3 wherein a wavelength of the light is a wavelength in the absorption spectrum of the known type of gas.

5. The method as recited in claim 3 wherein the step of providing light further comprises repeatedly switching the light on and off such that the step of detecting the light occurs both when the light is present in the chamber and when the light is absent in the chamber.

6. The method as recited in claim 3 further comprising the steps of providing a second sealed chamber containing a known reference gas having a known concentration such that the detecting step comprises alternatively detecting the amount of light in the sample chamber and detecting the amount of light in the second sealed chamber.

7. The method as recited in claim 6 wherein the step of providing light comprises positioning the light such that it is alternatively directed through the second sealed chamber containing the known reference gas and then directed through the chamber containing the gas sample mixture.

8. The method as recited in claim 3 wherein the step of providing light comprises providing a continuous stream of light from the light source through the chamber containing the gas sample mixture.

9. The method as recited in claim 3 wherein the step of comparing the CCS data comprises creating a database containing CCS data for the known type of gas at a range of known concentrations and at a range of known temperatures and alternatively accessing the CCS data from the database and the CCS data generated in step (j).

10. The method as recited in claim 3 wherein the step of comparing the CCS data comprises comparing each peak value of the CCS data generated in step (j) with a peak value of the CCS data of the known gas at known concentrations and at a known range of temperatures.

11. The method as recited in claim 3 wherein the step of comparing the CCS data comprises comparing a summation of all absolute value of the CCS data generated in step (j) with a summation of all absolute values of the CCS data of the known gas at known concentrations and at a known range of temperatures.

12. The method as recited in claim 3 wherein the step of comparing the CCS data comprises comparing a summation of each CCS data generated in step (j) multiplied by its corresponding time interval to a summation of the CCS data of the known gas of a known concentration at a known range of temperatures multiplied by its corresponding time interval.

13. The method as recited in claim 3 wherein the step of comparing the CCS data further comprises eliminating any CCS data having an absolute value less than a predetermined minimum CCS peak value.

14. An apparatus for determining the concentration of a known type of gas present in a gas sample mixture comprising:

(a) a gas chamber having an inlet and an outlet;

(b) an infrared light source connectable to a power supply and mounted within the gas chambers;

(c) a detector positioned in the gas chamber for detecting the light in the chamber and converting the light detected to an electric output signal which is a function of the light detected;

(d) an optical band pass filter also positioned within the chamber;

(e) a signal converter connectable to the detector which transforms the electrical output signal from analog output to digital output; and (f) a data acquisition and microprocessor means connected to the signal converter, the data acquisition and microprocessor means having the following functions:
   (i) measuring the output signal for four sequential instantaneous periods of time $t_1$, $t_2$, $t_3$, $t_4$;
   (ii) determining the relative difference between the output signals at $t_1$ and the output signal at $t_2$ which gives a change of output signal value $CS_1$;
   (iii) determining the relative difference between the output signal at $t_3$ and the output signal at $t_4$ which gives a change of output signal value $CS_2$;
   (iv) determining the relative difference between the change of output signal value $CS_1$ and the change of output signal value $CS_2$ which gives a change of the change of the output signal value $CCS_1$;
   (v) repeating the functions of (i) through (iv) to develop a plurality of CCS data which generates a pattern; and
   (vi) comparing the CCS data of function (v) to corresponding CCS data for the known type of gas at a range of known concentrations and at a range of known temperatures to determine the concentration of the known type gas in the sample mixture contained in the chamber.

15. The apparatus as recited in claim 14 further comprising a second reference gas chamber.

16. The apparatus as recited in claim 14 wherein the data acquisition and microprocessor means has a database containing CCS data of known gases having known concentrations at known ranges of temperatures.

* * * * *